Figure 1:
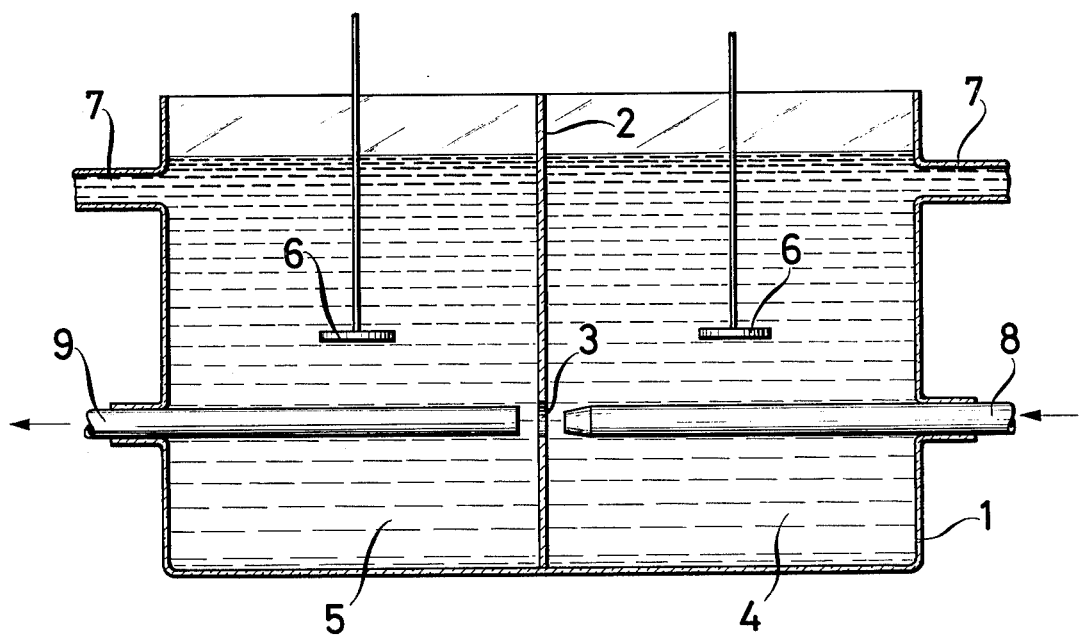

United States Patent [19]

Zimmermann et al.

[11] 4,081,340
[45] Mar. 28, 1978

[54] METHOD OF AND DEVICE FOR INCREASING THE PERMEABILITY OF THE SKIN OF CELLS OF LIVING BEINGS

[75] Inventors: Ulrich Zimmermann, Julich; Friedrich Riemann, Bad Salzuflen; Günter Pilwat, Julich, all of Germany

[73] Assignee: Kernforschungsanlage Julich Gesellschaft mit beschrankter Haftung

[21] Appl. No.: 762,320

[22] Filed: Jan. 25, 1977

Related U.S. Application Data

[63] Continuation-in-part of Ser. No. 546,771, Feb. 3, 1975, abandoned.

[30] Foreign Application Priority Data

Feb. 2, 1974 Germany .............................. 2405119

[51] Int. Cl.² .................... G01N 27/00; G01N 27/40
[52] U.S. Cl. ............................ 204/180 R; 204/299 R
[58] Field of Search .................... 204/180 R, 299; 23/230 B

[56] References Cited

U.S. PATENT DOCUMENTS

| 1,174,903 | 3/1916 | Schwerin | 204/180 R X |
| 1,229,150 | 6/1917 | Schwerin | 204/180 R X |
| 1,718,282 | 6/1929 | Fejes et al. | 204/180 R X |
| 2,085,898 | 7/1937 | Cardone | 204/180 R |
| 2,247,065 | 6/1941 | Pauli et al. | 204/180 R |
| 2,567,362 | 9/1951 | Berkman et al. | 204/180 R X |
| 3,118,876 | 1/1964 | Ukita et al. | 204/180 R X |

*Primary Examiner*—Arthur C. Prescott
*Attorney, Agent, or Firm*—Walter Becker

[57] ABSTRACT

A method of and device for increasing the permeability of the skin of cells of living beings, according to which the respective cells are introduced in the form of a suspension into an electrically conductive liquid. Thereby there is formed a physiological electrolyte solution which is passed into one of two chambers through a passage of a partition. This partition separates a container into these two chambers, each chamber having an electrode. This passage surrounds the focus of an electric field. The cells in the electrolyte solution are exposed to the electric field while passing from one chamber to the other chamber until macromolecules having a radius of at least 5 A are exchanged through the cell skin between the solution in the interior of the cells and the physiological electrolyte solution.

2 Claims, 2 Drawing Figures

METHOD OF AND DEVICE FOR INCREASING THE PERMEABILITY OF THE SKIN OF CELLS OF LIVING BEINGS

This is a continuation-in-part of copending application Ser. No. 546,771- Zimmermann et al filed Feb. 3, 1975 (Monday) now abandoned.

The present invention relates to a method of increasing the permeability of the skin of cells of living beings and means for practicing said method. The purpose of increasing the permeability of the skin of cells of living beings consists in introducing into the cells soluble substances which are characterized by desired chemical or physical properties in order to separate said substances from an aqueous solution. This brings about the advantage that catalytically effective substances are absorbed into the interior of the cells.

According to the present invention in a manner not previously known or suggested, cells of living beings are introduced into a solution containing complex formers or catalytically effective substances with an osmolarity lower than that of the cell contents. In view of the increased permeability of the cell skin, there occurs an exchange of the substance between the solution contained in the interior of the cell on one hand and the solution containing the complex formers or catalytically effective substances on the other hand. Thereupon the osmolarity of the solution containing the cells is increased by the addition of osmotically active substances such as calcium ions, sodium ions and potassium ions to the osmolarity of the cell contents of the originally introduced cells in connection with which the cell skin loses its permeability for the complex formers or catalytically effective substances contained in the interior of the cells, thereby enclosing said complex formers or catalytically effective substances. Cells treated in this way and containing complex formers are utilized for ionized substances characterized by chemical or physical properties being separated from an aqueous solution. In this connection, the cells containing the complex formers are introduced into the aqueous solution containing the ionized substances so that the ionized substances pass through the cell skin acting as a diaphragm and are converted by said complex formers into complexes which are difficult to dissociate or difficult to be dissolved. When the cells are separated from the aqueous solution, also the ionized substances bound in said cells are separated from the aqueous solution.

Cells containing catalytically effective substances are utilized for building up or for the decomposition of substances characterized by chemical properties and contained in an aqueous solution. The cells are inserted into the aqueous solution until the substances to be built up or to be decomposed and contained in the aqueous solution have, due to the permeability of the skin of the cells, moved into the interior of the cells. The building up or decomposition of the substances is completed, and the substances have moved through the skin of the cells into the aqueous solution whereupon the built-up or decomposed substances are separated from the aqueous solution in a manner known per se.

The suggested step for bringing about an increase in the permeability, according to which the cells are introduced into a solution with an osmolarity lower than the osmolarity of the cell contents is, however, time-consuming. The same is rather time-consuming because the increase in the permeability occurs only slowly. In addition thereto, a plurality of factors important for this method step have to be taken into consideration.

Moreover, if bacterial cells are employed as cells and it is necessary to remove the cell wall, an additional step known per se has to be resorted to in order to separate the cell wall.

It is an object of the present invention to provide a method of increasing the permeability of the skin of cells of living beings, which can be practiced in a simple, quick, and thus economical manner. Thus an increase in the permeability will be realized which makes possible a maximum exchange of macromolecules contained in the interior of the cells and in a solution into which the cells have been introduced. The macromolecules have a radius of at least 5 A. It is a further object of this invention to provide a method as set forth in the proceding paragraph in which the obtained increase in the permeability will be curable by a simple method.

It is still another object of this invention to provide a device for carrying out the method according to the invention.

These and other objects and advantages of the invention will appear more clearly from the following specification in connection with the accompanying drawings, in which:

FIG. 1 diagrammatically illustrates a section through a device according to the invention which comprises a container divided by a partition into two chambers.

Figure 2:
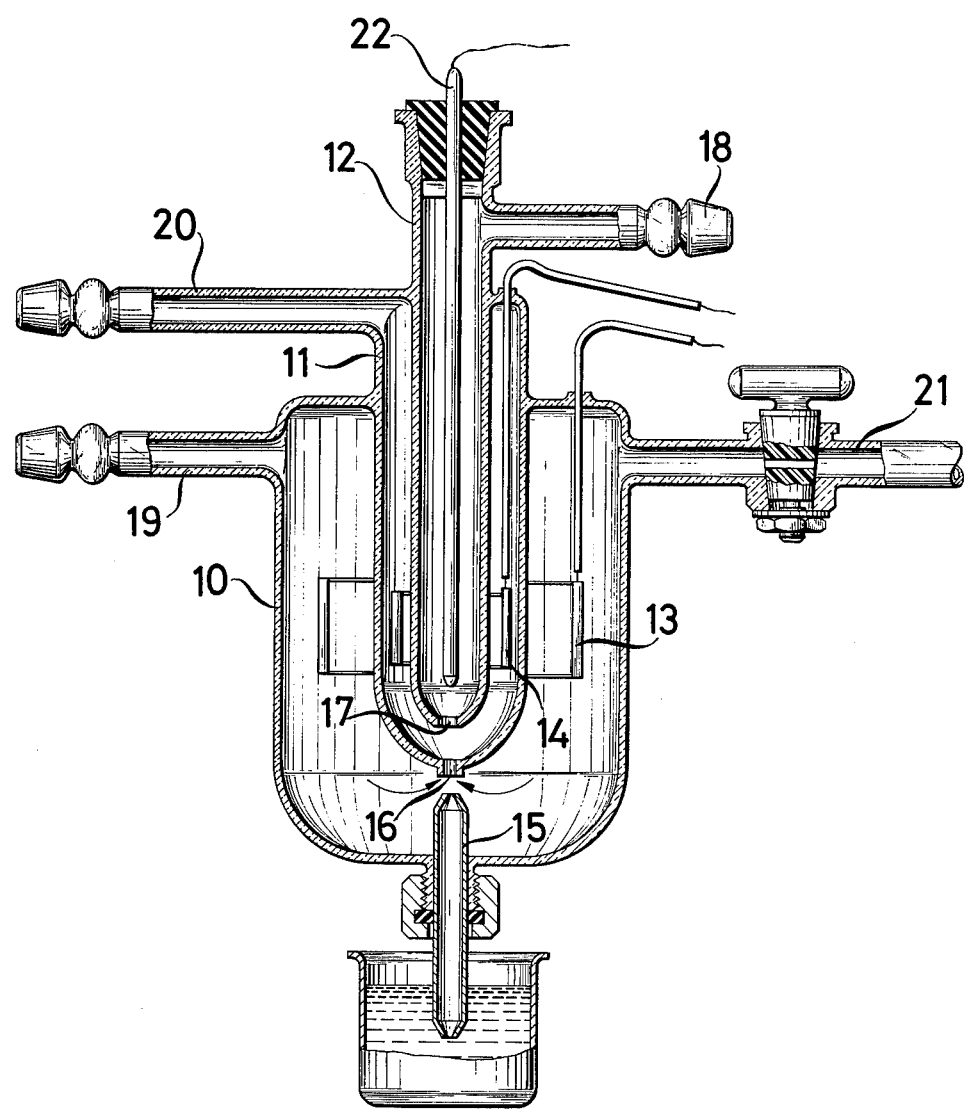

FIG. 2 illustrates a section through a device according to the invention which comprises three coaxially arranged containers.

The method according to the present invention for increasing the permeability of the skin of the cells of living beings is characterized primarily in the following. The cells are introduced into a liquid forming a suspension and having a temperature of between 0° and 25° C while being conductive for electric current and forming a physiological electrolyte solution. The thus formed physiological electrolyte solution which contains the cells is exposed to an electrical field until macromolecules having a radius of at least 5 A are exchanged through the cell skin acting as a diaphragm between the solution contained in the interior of the cell and the physiological electrolyte solution. The field intensity of the field bringing about the increase in permeability, expediently amounts to approximately from $10^3$ to $10^5$ V/cm.

The method according to the present invention can be carried out in a discontinuous as well as in a continuous manner. For carrying out the method in a discontinuous manner, a container having two electrodes arranged therein is filled with a physiological electrolyte solution as suspension which contains cells of living beings, and an electric pulse is emitted onto the electrolyte solution.

The method according to the invention when carried out in a continuous manner occurs in a container filled out with a physiological electrolyte solution having a constant electrical field applied to the electrodes of said electrolyte solution. The physiological electrolyte solution containing the cells as suspension is passed through said electrical field. This is advantageously carried out by feeding fresh physiological electrolyte solution containing the cells as suspension in a continuous manner into said container at the same time the electrolyte solution containing the cells and exposed to the electrical field is withdrawn from the container. At the same time, the heat generated in the electrical field in the electrolyte solution is withdrawn. A highly advantageous method according to the invention consists in that the physiological electrolyte solution which contains the cells as suspension is passed through the focus of a focused electrical field. In this way a better exploitation of the electrical field will be realized, and at the same time it will be assured that the cells which have been carried through the electrical field will all be exposed to an approximately identical field intensity.

The time that the cells stay in the electrical field bringing about the increase in the permeability, as necessary for increasing the permeability of the cell skin, is very short. Thus cells with increased permeability of the cell skin can be prepared in a simple manner and quickly and additionally at a high yield.

An advantageous modification of the method according to the present invention consists in that the physiological electrolyte solution which contains the cells passes through an opening surrounding the focus of the electrical field. This opening is provided in a wall formed of electrically non-conductive material and being arranged between the electrodes of the electrical field. In this way, a still better exploitation of the electrical field will be realized while all cells are exposed to practically the same electrical field. At the same time it will also be brought about that the exchange of macromolecules through the cell skin acting as diaphragm will occur even more completely. This will be recognized for instance when utilizing erythrozytes, by way of the discoloration of the electrolyte liquid in view of hemoglobin exiting from the interior of the cell and by the discoloration of the erythrozytes.

The method according to the invention is advantageously carried out by a device comprising a container divided into two chambers by a partition. A passage in the partition has a diameter of at least 20 μm. The partition is formed of electrically nonconductive material such as glass or the like. In the chambers there are electrodes respectively arranged one in each chamber. The container wall surrounding said chambers is provided with conduit connections for feeding physiological electrolyte solutions. Into one chamber there extends a feeding nozzle passing through the container wall and directed to said passage. The feeding nozzle is intended for the physiological electrolyte solution containing the cells. Into the other chamber there extends a suction line for the physiological electrolyte containing the cells. The suction line extends through the container wall and is likewise directed toward said passage.

For carrying out the method according to the invention, the diameter and the length of the passage and the electrical field applied to the electrodes depending on the desired flow-through are so dimensioned that the desired increase in the permeability of the cell skin will be effected.

An advantageous modification of the device for carrying out the method of the invention consists therein that three containers are provided which are formed of an electrically non-conductive material such as glass or the like. The containers are coaxially arranged with regard to each other so as to form an outer chamber, an intermediate chamber and an inner chamber. The outer chamber is provided with three conduit connections for feeding physiological electrolyte solution and for venting purposes. In the outer container there is provided an electrical passage for the electrodes arranged in the outer chamber. In the center of the bottom of the outer container there is provided a nozzle extending into said outer container for feeding thereinto the physiological electrolyte solution containing the cells. The upper part of the intermediate container is provided with a conduit connection for feeding into said intermediate container a physiological electrolyte solution. The upper portion of the intermediate container is furthermore provided with a passage for passing therethrough the inner electrodes coaxially arranged in the intermediate container with regard to the outer electrodes. The intermediate container at the bottom has a passage located opposite the opening of the feeding nozzle and having a diameter of at least 20 μm. In the upper portion of the inner container there is provided a conduit connection for withdrawing electrolyte solution containing the cells, and there is furthermore provided a passage for a thermo element. The inner container has its bottom provided with an opening which is located opposite to the opening of the feeding nozzle and opposite to the passage in the bottom of the intermediate container. After the catalytic substances have been received by the interior of the cells, the increase in the permeability of the skin of the cells is curable by heating the solution containing the cells for a period of from 1 to 2 hours to a temperature between 15° and 40° C. In other words, the increased permeability in this way will be restored to its previous permeability. When utilizing bacterial cells, the cells are expediently heated to a temperature of approximately 20° C, and when utilizing erythrozytes, the latter are expediently heated to a temperature of approximately 37° C. Due to the fact that the increased permeability of the cell skin is curable, the cells are usable for receiving macromolecules of various types and thus for various purposes of application.

The cells of living beings made in conformity with the method according to the invention are advantageously also applicable in methods for separating ionized substances. These substances are characterized by chemical or physical properties such as heavy metal ions or the like, separated from a dissolved mixture of substances contained in an aqueous solution. The solution comprises at least 0.5 mM magnesium ions and/or calcium ions and potassium ions such as sea water, fresh water, waste water or the like. Such separation may be effected by means of an organic or inorganic complex former aiding such separation and adapted to form a compound with the substances to be separated. The cells are inserted into a solution which contains the complex formers having an osmolarity which differs within limits from the osmolarity of the cell content of the original cells and from the osmolarity of the aqueous solution. This insertion takes place due to an exchange of substances through the cell skin acting as diaphragm. The exchange occurs until a balanced condition is attained between the solution contained in the interior of the cell and the solution containing the complex former. Then the cell content for all practical purposes corresponds to the solution containing the complex former. For purposes of curing the increase in the permeability, the solution containing the cells after being heated for approximately from one to two hours will be held at a temperature within the range of from 15° to 40° C. Subsequently thereto, the cells containing the complex formers are separated from the solution containing the complex former. For purposes of enriching the ionized substances contained in the aqueous solution, the cells are inserted into the aqueous solution until the ionized substances to be separated from the aqueous solution have moved through the cell skin acting as diaphragm into the interior of the cells and have been converted by the complex formers into complexes difficult to be dissociated and difficult to dissolve. In a second method step known per se, subsequently the cells are separated from the aqueous solution.

The cells of living beings made in conformity with the method of the invention are also applicable in an advantageous manner to methods for building up and decomposing substances characterized by chemical properties and dissolved in an aqueous solution containing at least 0.5 mM magnesium ions and/or calcium ions and/or potassium ions. This build-up and decomposition may be effected by means of catalytically effective substances aiding said build-up or said decomposition. In this connection, the cells are inserted into a solution containing catalytically effective substances. The osmolarity of this solution deviates in limits from the osmolarity of the cell content of the original cells and from the osmolarity of the aqueous solution. This insertion will continue until due to the increased permeability of the cell skin by the exchange of solution content in the interior of the cell and the solution containing the catalytically effective substances, the cell content corresponds for all practical purposes to the solution containing the catalytically effective substances. Thereupon the solution containing the cells after being heated for approximately one to two hours is held at a temperature within the range of from 15° to 40° C. Thereupon the cells containing the catalytically effective substances are separated from the solution containing the catalytically effective substances. For carrying out the method for building up or decomposing substances, the cells are inserted into the aqueous solution until the substances to be built up or to be decomposed contained in the aqueous solution have moved through the cell skin acting as diaphragm. The substances thus pass into the interior of the cells until the build-up or the decomposition of the substances have moved through the skin of the cells into the aqueous solution. The substances which have been built up or decomposed are then separated from the aqueous solution in a manner known per se.

Referring now to the drawing in detail, the container 1 is divided into two chambers 4 and 5 by means of a partition 2 which has a passage 3 therein. In each of said chambers 4 and 5 there is arranged an electrode 6. The container wall is provided with conduit connections 7 for separately passing physiological electrolyte solution into the chambers 4 and 5. For purposes of carrying out the method according to the invention, physiological electrolyte solution containing cells is conveyed from the outside to the chamber 4 through a feeding nozzle 8 and through the passage 3 which surrounds the focus of the electrical field and is then withdrawn from container 1 through withdrawal pipe 9 and is collected in a cooled collecting vessel (not shown in FIG. 1) which precedes the suction pump. The loss in physiological electrolyte solution is compensated for by way of the feeding lines 7.

FIG. 2 shows a further developed device according to the invention which comprises three coaxially arranged containers 10, 11 and 12 namely an outer container, an intermediate container and an inner container. In the outer and intermediate containers there are arranged electrodes 13 and 14. For carrying out the method according to the invention, the electrolyte solution containing the cells is conveyed through a jet capillary 15 to the outer chamber and through an orifice 16 provided in the intermediate container 11 and surrounding the electrical field and is further passed through an opening 17 in the inner container 12. This is effected by drawing in electrolyte solution through the connection or nipple 18. The drawn off cells are collected in a cooled collecting vessel not illustrated which precedes the suction pump. The loss in physiological electrolyte solution which occurs when carrying out the method in the device, is equalized through the conduit connections 19 and 20. The conduit connection 21 merely serves for venting the apparatus. In order to exclude any too strong heating and thereby damaging of the cells, a thermo element or thermo couple 22 is provided for controlling the temperature in the inner chamber.

EXAMPLE

Approximately 100 ml of fresh cattle blood was collected in an isotonic sodium citrate solution and the thus formed solution was centrifuged off in a centrifuge at 1200 g. Subsequently thereto, approximately 30 ml of the centrifuged off concentrated erythrozytes were washed twice while a corresponding centrifuging was effected. This washing was carried out in a 100 ml of a buffer solution which contained 150 mM NaCl, 16 mM KCl, 4 mM $MgCl_2$, 2 mM $CaCl_2$ and 5 mM Tris per liter and the pH value of which was adjusted to 7.4 by the addition of hydrochloric acid. Subsequently, the erythrozyte concentrate was diluted with buffer solution to which was added 1 mM adenosin-triphosphate per liter at a ratio of 10:3.

Thereupon the solution containing the erythrozytes was drawn through the jet capillary 15 of a device illustrated in FIG. 2. To this solution there was added at the same time a buffer solution which was cooled to 0° C and served as physiological electrolyte solution. The diameter and the length of the orifice 16 provided in the intermediate container 11, and the distance of the tip of the feeding jet capillary 15 from the orifice 16 amounted to 0.5 mm. A voltage of 350V was applied to the electrodes. The flow-through of the erythrozytes through the device was so selected that the inserted quantity of the erythrozytes had passed through the device within approximately 30 minutes. The erythrozytes collected in the collecting vessel were centrifuged off for about 15 minutes at a temperature of 0° and 13,000 g. From the centrifuged off erythrozytes, subsequently 0.5 ml were suspended in a solution of 5 ml buffer solution and 0.2 ml of an iodine $^{131}$-albumin solution having the specific activity thereof amounting to 0.1 mCi/ml, and held for about an hour at 0° C. Thereupon the solution was heated and for approximately 2 hours was held at 37° C. Thereupon the erythrozytes were centrifuged off for 15 minutes at 13,000 g, and the centrifuged off erythrozytes were washed twice in a buffer solution while each time a centrifuging off was effected. Said buffer solution contained 0.1% albumin as carrier.

The activity of the iodine $^{131}$-albumin remaining in the erythrozytes after the decomposition of the erythrozytes as measured in a triCarb-liquid scintillator. The measured activity corresponded to a 31% absorption of iodine $^{131}$-albumin by the erythrozytes from the solution containing iodine $^{131}$-albumin.

The concepts involved with wording, including "complex formers", "osmolarity" and "physical properties" actually do not have any role to play, or in other words, do not have any importance with the method of the present invention. Much more there is noted that these concepts were used for describing methods noted in the introductory paragraphs of the present case noted to represent the practical usefulness of the method according to this invention.

Thus, the aforementioned concepts do not concern directly the method of the present invention. The introductory paragraphs relate to disclosure of co-pending application Ser. No. 472,473-Zimmermann filed May 22, 1974 now included with a Continuation-in-part application Ser. No. 637,464-Zimmermann filed Dec. 3, 1975.

To clarify what is to be understood from the wording "complex formers", there is noted that the complex formers enter into compounds or compositions with materials characterized by way of physical and chemical characteristics. The following paragraphs will set forth more clearly the meaning of such terminology. Complex formers are also called masking means, and such complex formers are chemical materials which are used for formation of coordination compositions or compounds with respect to ions located together therewith in a solution. Complex formers as well as utilization thereof are known to every man skilled in the art. So, there is known for example that through introduction or insertion of complex formers there can be ions so bound in a solution that the ions do not disturb the evidence, detection or analysis of other ions likewise existing in the solution. Accordingly there exists also the designation "masking" for the occurrence or entry of these compositions. Organic compositions primarily or most of all are utilized as complex formers (or masking means) (for formation of Chelat complexes) as well as fluoride and cyanide which are also used for such purposes. The utilization of complex formers or masking means is an important aiding means for quantitative evaluation of a type of ion and analytic chemistry whereby there is not necessary any analytic separation of the ions.

From the foregoing representations there can be recognized that the complex formers enter into composition selectively with predetermined ions which means that they enter into composition with "material characteristically and notably ionized by way of chemical or physical characteristics". The description permits recognition that the concern with these materials involves those which differ by way of chemical or physical characteristics as to others, particularly those from which the same are to be separated.

Since accordingly as apparent from the foregoing statements, the complex formers as well as the utilization thereof for the average man skilled in the art can be preconditioned as being known. There can also be preconditioned that an average man skilled in the art who receives the teaching given by way of the present invention knows the complex formers must be used or inserted for separation of predetermined ions out of an ion mixture. Consequently and to this extent, the teaching of the present invention pertains to separation of all substances which can be bound by way of utilization of complex formers.

Complex formers or "chelating agents" which are embodied respectively according to the type of ions to be separated become introduced into cells of live or living things by utilization of osmotic forces in that the cells lose the content thereof by interchange of such cell content with the solution containing the complex formers or "chelating agents", whereupon the damage effected by way of the effect of the osmotic forces in the bubbles formed out of the cells by way of interchange of the cell content becomes healed again by way of addition of osmotic active materials in the cell-containing solution.

The concern hereby involves such ionized materials which are transformed through complex formers into complex compounds which are difficult to dissociate or difficult to dissolve. Which materials could be transformed by way of complex formers into such complexes is known to the average man skilled in the art.

With respect to the concept of "osmolarity" there must be clarified which function is attributed in the individual method steps as to the different osmolarities of the solutions in which the cells of living things that are to be treated can be found. For this purpose attention is directed to statements that the cells are introduced into a solution for production of membrane vesiculs of which the osmolarity relative to osmolarity of cell content is so low that by way of the osmatic pressure arising in the cells and becomes changed, the cell membrane becoming partially damaged and thereby effecting an increase in permeability; in other words, there is noted that boundaries between the osmolarity of the cell content and the osmolarity of the aqueous solution must be noted and knowingly becomes exceeded with the low osmolarity between the cell content and the solution. The permeability increase knowingly brought about as to the membranes has a consequence that a material interchange occurs between the cell content and the solution with the low osmolarity in which the catalytically effective materials, the enzymes, are located. First thereby is it possible that the materials catalytically effective provide a greater diameter coming through the membrane into the interior of the cells. Nothing further needs to be stated in the present case so that there is to be understood that then when a change of permeability of the cell membranes of the cells is not intended, the cells become kept in isotone or quasi-isotone solutions, which means those with an osmolarity corresponding to the osmolarity of the cell content. There is repeated that the wording or concepts are not of importance with the present case. First there must be stressed the essence of the present invention and for clarification of the method of the present case the statements of the following paragraphs are noted in particular.

With the aforementioned methods with which complex formers catalytically effect materials, enzymes become enclosed in cells and become effected as indicated by the foregoing that the permeability increase occurs by way of effect of osmatic pressure. The necessary method step as set forth in detail in the present U.S. description can be considered complex and time consuming. The object of the present invention accordingly is to create a method through which the permeability of the cell membranes of cells of living things becomes increased quickly and in a simple and economical manner and that simultaneously the aforementioned complex method step can be replaced thereby. This object is the basis of the present invention. For solution of this object, the inventors have formed a completely novel procedure consisting therein that the cells are introduced as a suspension in a physiological electrolyte solution whereupon the electrolyte solution becomes subjected to an electric field so long until macromolecules provide a radius of at least 5 A become interchanged through the cell skin effective as a membrane between the solution contained inside the cell and the physiological electrolyte solution. Fields strengths of approximately $10^3$ and $10^5$ V/cm become utilized. The average man skilled in the art should be aware of which macromolecules are involved depending upon selection of the cells thereby in an individual case. In the case of the application or utilization of the method according to the present invention as to the increase of permeability of the membrane of "Erythrozytes" the concern involved with the macromolecules involves hemoglobin as set forth in the present specification. With the method according to the present invention there is clear that the concern does not involve utilization of osmatic pressure. The concern, however, also does not involve a method of a type of the art of record in what is believed to be erroneously understood in what is involved with the present invention; with the cited references by way of utilization of a relatively low electric voltage there is noted that ions begin to wonder through the membranes of the cells including particularly ions for which the membranes of the cells is readily permeable. For this purpose attention is directed to the lines 82–86 on Page 2 of the U.S. Pat. No. 1,229,150-Schwerin as well as lines 43–45 in column 4 of U.S. Pat. No. 2,547,231-Sartakoff; lines 72–75 column 3 of U.S. Pat. No. 3,168,377-Williams. In comparison with the present inventive method there are utilized field strengths in the range between $10^3$ and $10^5$ V/cm and thereby a permeability increase of the membrane of the cells becomes effected whereby the membrane of the cells also becomes permeable for macromolecules and higher ion flow becomes attained around greater magnitude. There has been shown that by way of the method of the present invention changes are effected in the cell membrane which lead to permeability though being capable of being healed out again so that the method according to the present invention can be used in place of the method step mentioned previously with which by way of effect of the osmatic pressure the permeability of the cells becomes increased. From the foregoing statements, there is apparent that the present invention in novel beyond any doubt and represents an advance in the art over the previously utilized method for increase of permeability. No doubt can exist that the method of the present invnntion is also inventive since the average man skilled in the art when relying on the references cited would not find any showing or suggestion to make obvious the teaching of the present invention.

There is stressed the feature that an electric field of a field strength of approximately $10^3$ to $10^5$ V/cm becomes utilized.

The sample embodiments set forth both the composition of the electrolyte, the quantity of the erythrosytes suspending in electrolyte, the utilized field strength, as well as the time while the cells become subjected to the electric field. Attention is directed to the description in which the buffer solution has already been set forth. Moreover, an average man skilled in the art knows that the concern with a buffer solution involves combination of a weak acid and salts thereof (mostly sodium salt) becoming added to a chemical reactive solution in order to keep the pH value, important for chemical reactions, as stable as possible against addition of strong acids or bases. In the present case the addition of buffer solutions serves the purpose to maintain stable the solution contained in the cells for protection of the cells.

Clarification of electrical field strength to be utilized will become apparent from the following comments:

The Takeya, et al disclosure (U.S. Pat. No. 3,751,356) describes a method and an apparatus having as a goal extraction of organic materials from a solution. These materials are contained in the solution in dissolved form, or in other words, as ions, and the solution consists of water and an organic solvent. This extraction occurs through applying of an electrical voltage; according to the teaching of Takeya, the solution is introduced into a dialyser (apparatus). Dialysis membranes are provided in this apparatus; the dialysis membranes are synthetic membranes (cellulose) used in a manner known to the average man skilled in the art. These synthetic membranes are utilized only as a working means with the known method. These membranes are not subjected to any change while carrying out the known method as is self-understood for the average man skilled in the art.

The present invention pertains to a method for increasing permeability of the skin (of the membrane) of cells of living things; the permeability increase under these conditions should be so determined that the changes of the cell skin are healed-out again. The goal of the method according to the present invention is to make the membrane of cells of living things reversibly conductive. There should not be necessary any particular emphasis that membranes of cells of living things are not related in the slightest way with synthetic dialysis membranes as used by Takeya. The cell membranes involve biological membranes consisting of proteins and lipids (Lipiden); these biological membranes provide characteristics that previously could not be attained with synthetic membranes. Thus, the features of the method in accordance with the present invention cannot be recognized at all in the utilization of dialysis membranes, while carrying out the teaching of Takeya. Utilization of an electrical field for supporting a dialysis procedure as has been known for a long time cannot be taken by the average man skilled in the art to provide in any way any showing or suggestion as to the method according to the present invention. Under these circumstances, the electrical field is not used to influence the dialysis membrane in any manner. Thus no mention can be made accordingly that the features of the present invention are made obvious by the teaching of Takeya. Beyond any doubt the method of the present invention is novel, an advance and inventive since the average man skilled in the art has not provided or been provided with any other suggestion for utilization of electrical voltage for changing of biological cell membranes.

On the basis of the statements in the foregoing paragraphs there exists sufficient inventive height.

The present invention has as a goal the increase of the permeability of the membranes of living cells of living things. This increase of the permeability is to be brought about in accordance with the object that is the basis of the present invention, whereby the permeability is capable of being healed-out in a simple method step.

The following features are set forth by applicants for resolving the object that is the basis of the present invention:

(a) The cells of living things for which the cell membrane is to be changed in the prescribed manner are introduced into a physiological solution which is simultaneously usable as an electrolyte fluid, while the temperature of the solution lies between 0° and 25° C.

(b) The electrolyte solution containing the cells (and accordingly also the cells) are subjected to an electrical field having a field strength between approximately $10^3$ through $10^5$ volts per centimeter.

(c) The electrolyte solution (and accordingly the cells therewith) are subjected to the electrical field as long as molecules with a diameter of at least 5 A are interchanged between the cell interior and the electrolyte solution surrounding the cell, such interchange occurring through the cell membranes changed as a consequence of the applied electrical field.

In order to set forth that sufficient disclosure and description exists for the average man skilled in the art on the basis of the method consisting of the steps (a) - (c) in accordance with the present invention, in referring to sample embodiments, there can additionally be noted the following:

With respect to the method step (a), the average man skilled in the art does not have to be provided with any directions when living cells of living things are to be introduced into a physiological solution serving as an electrolyte solution. No special statements are necessary about the concentration of the cells in the electrolyte, particularly since the increase in permeability sought through the method in accordance with the present invention is attained independently of the concentration of the cells in the electrolyte solution. Furthermore, there is set forth in the same embodiment of the specification how such an electrolyte solution is produced containing the cells based on 100 ml beef blood (fresh cattle blood).

As to the method step (b), the feature of subjecting the electrolyte solution to an electrical field of the aforementioned field strength does not require any further statements for the average man skilled in the art. Additionally there is set forth in the specification that the application of the electrical field can occur continuously or discontinuously. There is set forth in detail in the specification how one is to proceed with a continuous procedural manner. This procedural manner was utilized also in the sample embodiment.

With respect to the method step (c), the dwell time for the cells in the electrical field which is necessary for increasing the permeability of the cell membranes is very short. Therefore the average man skilled in the art is provided with a clear teaching that this dwell time is so determined that molecules with a radius of at least 5 A are just interchanged through the cell membrane that became conductive through application of the electrical field. In the case of utilization of the method in accordance with the present invention for erythrocytes, the interchange of the materials is recognizable by way of coloring of the erythrocytes and also is recognizable by coloring of the electrolyte fluid.

These statements convey to the average man skilled in the art sufficient teaching to put him in a position to carry out the method in accordance with the present invention so that the provided permeability increase is attained. If the average man skilled in the art proceeds in this manner using the teaching in accordance with the present invention, then there is assured simultaneously that the permeability increase again is capable of being healed-out.

To facilitate understanding of this terminology, there is noted that erythrocyte literally means a red blood cell or corpuscle. The portion of the word "erythro-" means red, and the portion "-cyte" means hollow fossil or cell, and therefore a red blood cell is to be taken as the meaning of this word. In hystology the word erythrocyte according to the 1974, "McGraw-Hill Dictionary of Scientific and Technical Terms" means a type of blood cell that contains a nucleus in all vertebras but man and has hemoglobin in cytoplasm (also known as a red blood cell).

Applicants provided accurate statements for the average man skilled in the art in the sample embodiment; these statements concern the quantity of erythrocytes suspended in the electrolyte (30 ml electrocytes concentrate are thinned with buffer solution in a ratio of 10:3); an accurate statement is also made about the time (30 minutes) in which this suspension passes the electrical field which prevails between the tip of the supply nozzle 15 and the passage 16. Accordingly, all parameter values are set forth for the average man skilled in the art through which the aforementioned dwell time is determined since also the spacing between the tip of the supply nozzle 15 and the passage 16 is set forth at a value of 0.45 mm.

The method of the present invention serves for increasing the permeability of cell membranes; the method serves to replace the known method step with which the permeability of the cell membranes is increased through the effect of osmotic pressure. The attained permeability increase should be capable of being healed-out again. In other words, the field strength of the electrical field applied according to the method of the present invention as well as the time duration of the influence of the electrical field upon the cell is to be so determined that the material introduced into the cells after the permeability increase are enclosed through healing-out of the permeability increase. Accordingly, it is likewise a criterion for successfully carrying out the method according to the present invention that materials are enclosed in the cells on the basis of the features set forth in the specification. For this reason in the sample embodiment there has been set forth accordingly those measures which are necessary for enclosing of iodine $^{131}$-albumin including those measures necessary for proving this enclosure.

It is, of course, to be understood that the present invention is, by no means, limited to the specific showing in the drawings and the specific example set forth above, but also comprises any modifications within the scope of the appended claims.

What we claim is:

1. A method of increasing the permeability of the skin of cells of living beings, which includes in combination the steps of: introducing the respective cells in the form of a suspension into an electrically conductive liquid having a temperature of from 0° to 25° C and forming a physiological electrolyte solution, exposing the thus formed physiological electrolyte solution containing said cells to an electric field of predetermined strength until macromolecules having a radius of at least 5 A are exchanged through the skin acting as diaphragm for said cells between the solution in the interior of said cells and the physiological electrolyte solution.

2. A method im combination according to claim 1, which includes the step of passing the physiological electrolyte solution containing said cells through the focus of a focused electric field of $10^3$ to $10^5$ V/cm strength.

* * * * *